United States Patent [19]
Huebner

[11] Patent Number: 5,961,555
[45] Date of Patent: Oct. 5, 1999

[54] MODULAR SHOULDER PROSTHESIS

[76] Inventor: Randall J. Huebner, 18650 SW. Hart Rd., Aloha, Oreg. 97007

[21] Appl. No.: 09/040,504

[22] Filed: Mar. 17, 1998

[51] Int. Cl.$^6$ ........................................................ A61F 2/40
[52] U.S. Cl. .............................................................. 623/19
[58] Field of Search ................................. 623/19, 18, 22, 623/23

[56] References Cited

U.S. PATENT DOCUMENTS

| | | |
|---|---|---|
| 2,682,265 | 6/1954 | Collison . |
| 2,719,522 | 10/1955 | Hudack . |
| 2,765,787 | 10/1956 | Pellet . |
| 2,781,758 | 2/1957 | Chevalier . |
| 2,785,673 | 3/1957 | Anderson . |
| 3,064,645 | 11/1962 | Ficat et al. . |
| 3,067,740 | 12/1962 | Haboush . |
| 3,102,536 | 9/1963 | Rose et al. . |
| 3,658,056 | 4/1972 | Huggler et al. . |
| 3,670,724 | 6/1972 | Bosacco . |
| 3,694,820 | 10/1972 | Scales et al. . |
| 3,782,373 | 1/1974 | Smythe . |
| 3,806,957 | 4/1974 | Shersher . |
| 3,814,089 | 6/1974 | Deyerle . |
| 3,818,512 | 6/1974 | Shersher . |
| 3,859,669 | 1/1975 | Shersher . |
| 3,863,273 | 2/1975 | Averill . |
| 3,874,003 | 4/1975 | Moser et al. . |
| 3,906,550 | 9/1975 | Rostoker et al. . |
| 3,916,451 | 11/1975 | Buechel et al. . |
| 3,918,441 | 11/1975 | Getscher . |
| 3,974,527 | 8/1976 | Shersher . |
| 3,979,778 | 9/1976 | Stroot . |
| 3,987,499 | 10/1976 | Scharbach et al. . |
| 4,004,300 | 1/1977 | English . |
| 4,030,143 | 6/1977 | Elloy et al. . |
| 4,040,131 | 8/1977 | Gristina . |
| 4,042,980 | 8/1977 | Swanson et al. . |
| 4,051,559 | 10/1977 | Pifferi . |
| 4,115,875 | 9/1978 | Rambert et al. . |
| 4,261,062 | 4/1981 | Amstutz et al. . |
| 4,404,691 | 9/1983 | Buning et al. . |
| 4,406,023 | 9/1983 | Harris . |
| 4,430,761 | 2/1984 | Niederer et al. . |

(List continued on next page.)

FOREIGN PATENT DOCUMENTS

| | | |
|---|---|---|
| 0000549A1 | 2/1979 | European Pat. Off. . |
| 0017743A1 | 10/1980 | European Pat. Off. . |
| 0098224A1 | 1/1984 | European Pat. Off. . |
| 0145939A2 | 8/1985 | European Pat. Off. . |
| 0163121A1 | 12/1985 | European Pat. Off. . |
| 0190981A1 | 8/1986 | European Pat. Off. . |
| 0198163A2 | 10/1986 | European Pat. Off. . |
| 0201407A1 | 11/1986 | European Pat. Off. . |
| 0243298A2 | 10/1987 | European Pat. Off. . |
| 0278807A2 | 8/1988 | European Pat. Off. . |
| 0339530A2 | 2/1989 | European Pat. Off. . |

(List continued on next page.)

OTHER PUBLICATIONS

Moeckel et al., "Modular Hemiarthroplasty for Fractures of the Proximal Part of the Humerus," *The Journal of Bone and Joint Surgery, Incorporated*, vol. 74–A, No. 6, pp. 884–889, Jul. 1992.

Fenlin, Jr. et al., "Modular Total Shoulder Replacement: Design Rationale, Indications, and Results," *Clinical Orthopaedics and Related Research*, No. 307, pp. 37–46, © 1994.

(List continued on next page.)

*Primary Examiner*—David J. Isabella
*Attorney, Agent, or Firm*—Kolisch, Hartwell, Dickinson, McCormack & Heuser

[57] ABSTRACT

A modular shoulder prosthesis including a head having a semi-spherical articulation surface bounded by an articular margin disposed in an articular plane generally normal to a head axis. The head further includes a backside disposed opposite the articulation surface and separated from the articulation surface by the articular margin. The prosthesis also includes a stem portion with a proximal end and a distal shaft for insertion into a medullary canal along a shaft axis. A coupling structure is adapted to removably attach the head to the stem through motion in the articular plane.

25 Claims, 9 Drawing Sheets

U.S. PATENT DOCUMENTS

| | | |
|---|---|---|
| 4,459,708 | 7/1984 | Buttazzoni . |
| 4,488,319 | 12/1984 | von Recum . |
| 4,532,660 | 8/1985 | Field . |
| 4,550,450 | 11/1985 | Kinnett . |
| 4,578,081 | 3/1986 | Harder et al. . |
| 4,624,674 | 11/1986 | Pappas et al. . |
| 4,645,506 | 2/1987 | Link . |
| 4,655,778 | 4/1987 | Koeneman . |
| 4,676,797 | 6/1987 | Anapliotis et al. . |
| 4,693,723 | 9/1987 | Gabard . |
| 4,693,724 | 9/1987 | Rhenter et al. . |
| 4,698,063 | 10/1987 | Link et al. . |
| 4,822,370 | 4/1989 | Schelhas . |
| 4,840,632 | 6/1989 | Kampner . |
| 4,842,606 | 6/1989 | Kranz et al. . |
| 4,865,605 | 9/1989 | Dines et al. . |
| 4,865,609 | 9/1989 | Roche . |
| 4,895,572 | 1/1990 | Chernoff . |
| 4,904,266 | 2/1990 | Barber . |
| 4,908,032 | 3/1990 | Keller . |
| 4,919,669 | 4/1990 | Lannelongue . |
| 4,919,670 | 4/1990 | Dale et al. . |
| 4,932,974 | 6/1990 | Pappas et al. . |
| 4,963,155 | 10/1990 | Lazzeri et al. . |
| 4,986,833 | 1/1991 | Worland . |
| 4,995,883 | 2/1991 | Demane et al. . |
| 5,002,580 | 3/1991 | Noble et al. . |
| 5,002,581 | 3/1991 | Paxson et al. . |
| 5,030,234 | 7/1991 | Pappas et al. . |
| 5,032,130 | 7/1991 | Schelhas et al. . |
| 5,074,879 | 12/1991 | Pappas et al. . |
| 5,080,676 | 1/1992 | May . |
| 5,080,685 | 1/1992 | Bolesky et al. . |
| 5,108,437 | 4/1992 | Kenna . |
| 5,108,452 | 4/1992 | Fallin . |
| 5,116,379 | 5/1992 | McLardy-Smith . |
| 5,135,529 | 8/1992 | Paxson et al. ............................ 623/23 |
| 5,169,401 | 12/1992 | Lester et al. . |
| 5,181,928 | 1/1993 | Bolesky et al. . |
| 5,207,682 | 5/1993 | Cripe . |
| 5,261,915 | 11/1993 | Durlacher et al. . |
| 5,282,865 | 2/1994 | Dong . |
| 5,286,260 | 2/1994 | Bolesky et al. . |
| 5,314,479 | 5/1994 | Rockwood, Jr. et al. . |
| 5,336,268 | 8/1994 | Rispeter .................................... 623/23 |
| 5,342,363 | 8/1994 | Richelsoph . |
| 5,358,526 | 10/1994 | Tornier . |
| 5,370,706 | 12/1994 | Bolesky et al. . |
| 5,405,403 | 4/1995 | Mikhail . |
| 5,489,309 | 2/1996 | Lackey et al. . |
| 5,507,817 | 4/1996 | Craig et al. .............................. 623/23 |
| 5,507,818 | 4/1996 | McLaughlin ............................. 623/23 |
| 5,549,682 | 8/1996 | Roy . |
| 5,580,352 | 12/1996 | Sekel . |
| 5,591,233 | 1/1997 | Kelman et al. . |
| 5,645,607 | 7/1997 | Hickey ..................................... 623/23 |
| 5,658,340 | 8/1997 | Muller et al. . |
| 5,800,560 | 9/1998 | Draenert .................................. 623/23 |

FOREIGN PATENT DOCUMENTS

| | | |
|---|---|---|
| 0393608A2 | 10/1990 | European Pat. Off. . |
| 0501207A1 | 9/1992 | European Pat. Off. . |
| 0611225A1 | 8/1994 | European Pat. Off. . |
| 0617934A1 | 10/1994 | European Pat. Off. . |
| 0622062A1 | 11/1994 | European Pat. Off. . |
| 0634154A1 | 1/1995 | European Pat. Off. . |
| 0639359A1 | 2/1995 | European Pat. Off. . |
| 0679375A1 | 11/1995 | European Pat. Off. . |
| 0715836A1 | 6/1996 | European Pat. Off. . |
| 2225141 | 4/1974 | France . |
| 2378505 | 8/1978 | France . |
| 2567019 | 1/1986 | France . |
| 2574283 | 6/1986 | France . |
| 2579454 | 10/1986 | France . |
| 2606273 | 5/1988 | France . |
| 2619502 | 2/1989 | France . |
| 2634371 | 1/1990 | France . |
| 2652498 | 4/1991 | France . |
| 2664809 | 1/1992 | France . |
| 2670108 | 6/1992 | France . |
| 2689756 | 10/1993 | France . |
| 2689757 | 10/1993 | France . |
| 2689758 | 10/1993 | France . |
| 2699400 | 6/1994 | France . |
| 2705558 | 12/1994 | France . |
| 2576793 | 8/1996 | France . |
| 2737107 | 1/1997 | France . |
| 2015324 | 11/1971 | Germany . |
| 2400650 | 7/1974 | Germany . |
| 3023354A1 | 4/1981 | Germany . |
| 3329978A1 | 3/1985 | Germany . |
| 3415934A1 | 10/1985 | Germany . |
| 4320086C2 | 10/1995 | Germany . |
| 19548154A1 | 6/1997 | Germany . |
| 1279629A1 | 12/1986 | U.S.S.R. . |
| 1443470 | 7/1976 | United Kingdom . |
| 1521679 | 8/1978 | United Kingdom . |
| 1531487 | 11/1978 | United Kingdom . |
| 2070939 | 9/1981 | United Kingdom . |
| 2223172 | 4/1990 | United Kingdom . |
| WO83/02555 | 8/1983 | WIPO . |
| WO91/18559 | 12/1991 | WIPO . |
| WO94/15551 | 7/1994 | WIPO . |
| WO96/17553 | 6/1996 | WIPO . |
| WO96/41597 | 12/1996 | WIPO . |

OTHER PUBLICATIONS

The Neer II Total Shoulder System, The 3M™ Modular Shoulder System brochure, Wright Medical Technology, Inc., © 1995.

Capanna et al., "A Humeral Modular Prostheses for Bone Tumour Surgery: A Study of 56 Cases," *International Orthopaedics,* vol. 10, No. 4, pp. 231–238, 1986.

Fenlin Total Shoulder brochure, Zimmer, Inc., © 1998.

The BiAngular Shoulder brochure, Biomet, Inc., © 1989.

Bio–Modular Total Shoulder brochure, Biomet, Inc., © 1990.

The Geometry of the Humeral Head and the Design of Prosthesis, Roberts et al., *The Journal of Bone and Joint Surgery,* vol. 73–B, No. 4, Jul. 1991.

Buechel–Pappas Total Shoulder System instructions, Oct. 1991.

Total Shoulder Arthroplast: Factors Influencing Prosthetic Sizing, Iannotti et al., University of Pennsylvania Medical Center, 1994.

Retroversion of the Proximal Humerus in Relationship to Prosthetic Replacement Arthroplasty, Pearl et al., *J. Shoulder Elbow Surg.,* vol. 4, No. 4, Jul./Aug. 1995.

Total Shoulder Arthroplasty: Pearls and Pitfalls in Surgical Technique, Romeo, *Seminars in Arthroplasty,* vol. 6, No. 4, Oct. 1995.

Global Total Shoulder Arthroplasty System brochure, 1995.

Four Part Humeral Fracture Repair description, DePuy, Inc., 1995.

Shoulder Prosthesis description, Tornier, undated.

Intermedics Orthopedics Select Shoulder System, Intermedics Orthopedics, Inc., undated.

The Aequalis Shoulder Prosthesis brochure, Tornier, Inc., undated.

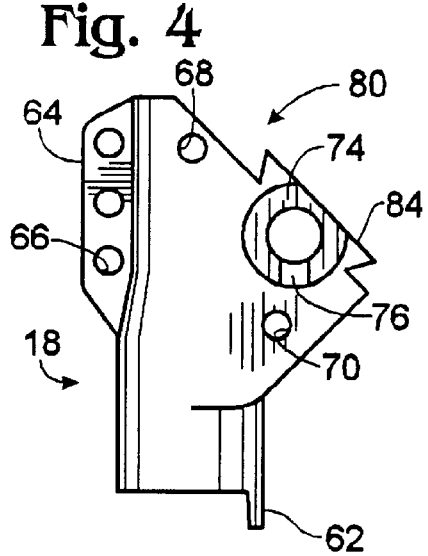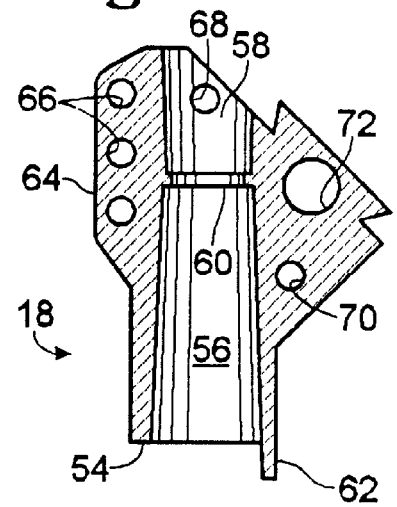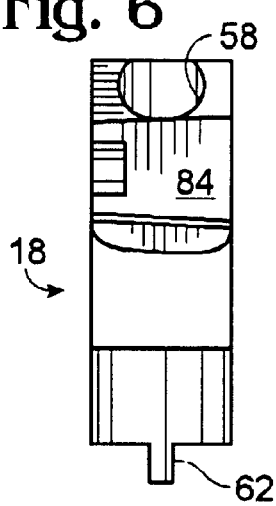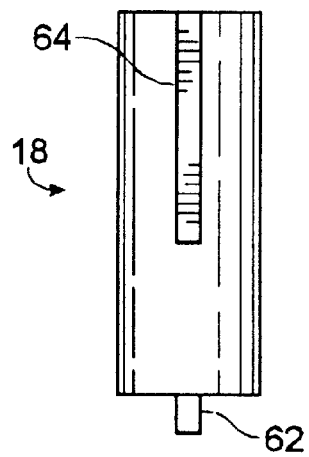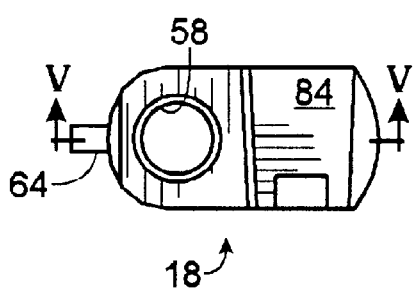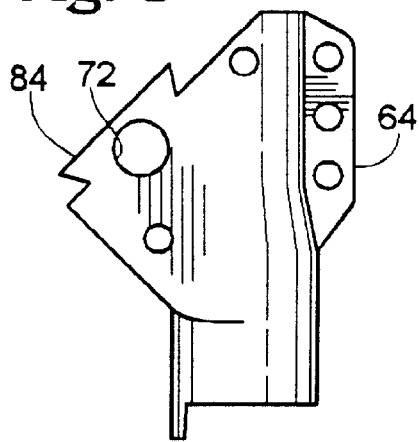

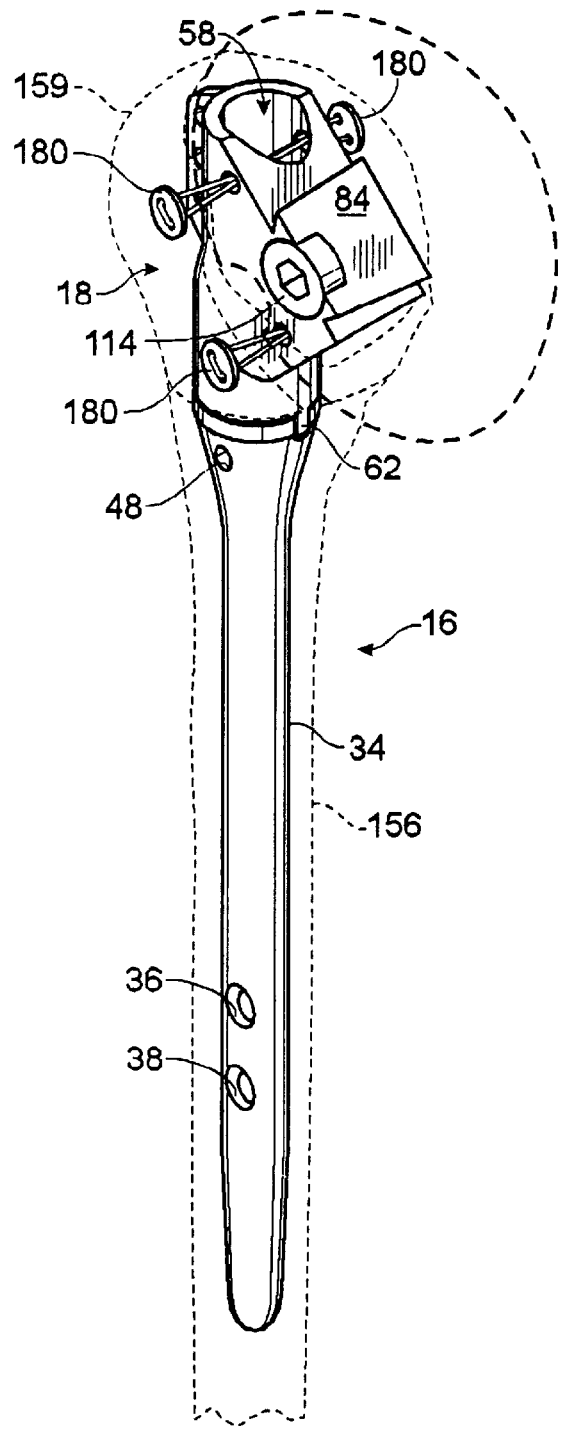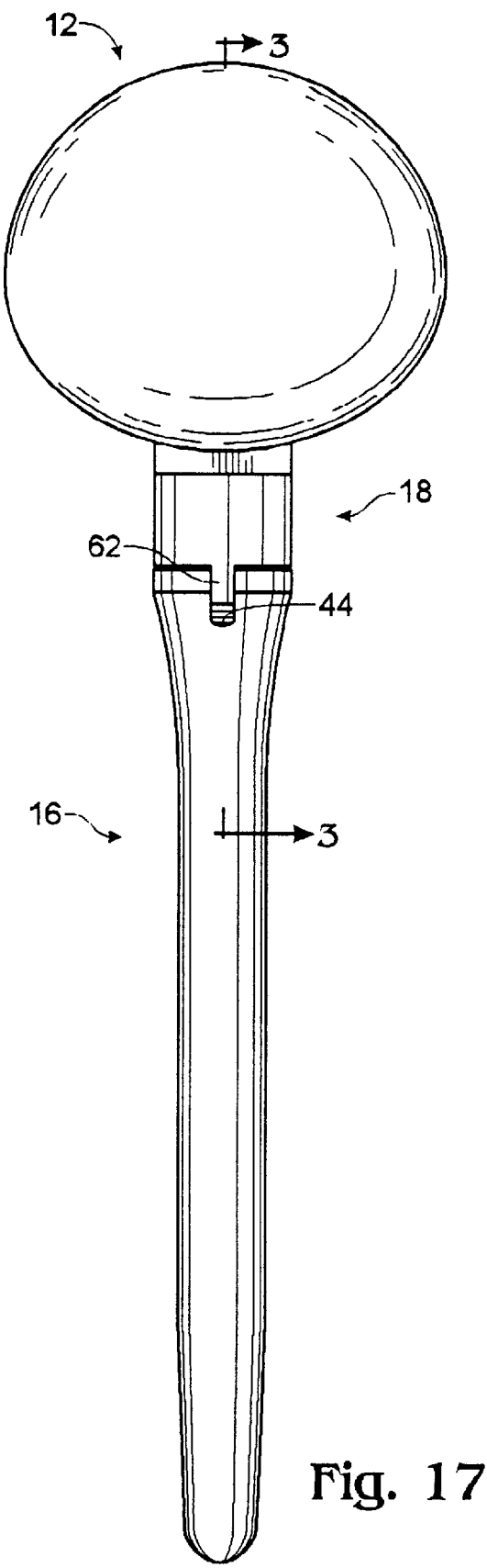

MODULAR SHOULDER PROSTHESIS

This invention relates generally to bone prostheses and more particularly to a modular shoulder prosthesis.

BACKGROUND OF THE INVENTION

When a joint, such as the hip or shoulder, becomes impaired due to arthritis, disease or trauma, it is sometimes necessary to replace all or part of the joint with a prosthesis to restore function. For instance, hip replacement, where a prosthesis is provided to replace the femoral head and in some cases all or part of the acetabulum, has become a common procedure to treat femoral head fractures and arthritis in elderly patients. As a result of anatomical constraints and challenges in the shoulder, shoulder implants have historically been much less successful and less common than hip replacements. Recently, however, shoulder arthroplasty has emerged as an accepted treatment for severe arthritis and humeral head fractures.

As a consequence of the increasing acceptance of shoulder prostheses, many different devices have been developed to address various problems that have arisen and to offer additional benefits and features. In the simplest form, a shoulder prosthesis is formed as a single piece with a head to articulate with the glenoid cavity, and a stem to extend down the medullary canal of the humerous and support the head. While simple to construct, unitary implants do not offer any adjustability to accommodate the natural variations in size and geometry that occur among joints of different patients. To accommodate these variations, a large stock of devices must be manufactured and maintained to insure that an adequate match can be achieved during an operation. Stocking the large number of devices is a significant expense with one-piece designs, and in some cases a surgeon may not be provided with sufficient flexibility to achieve an ideal fit to the patient.

To avoid the expense of maintaining a large stock of single-piece prosthetics and to provide increased flexibility to surgeons, many shoulder implant makers have gone to a modular design that is assembled during the operation from two or three pieces. These pieces include a head to articulate with the glenoid and a stem structure on which the head is mounted and secured to the bone. In some cases, the stem includes a separate body portion disposed between the head and an intermedullary portion of the stem that extends down the medullary canal. By utilizing a modular design, a wide variety of devices can be assembled from only a few pieces, thus providing increased flexibility to accommodate anatomical variation and eliminating much of the cost associated with maintaining a large selection of one-piece devices.

One drawback of existing modular implants is the difficulty of reliably and easily attaching the pieces together. With existing designs, the pieces are most commonly held together with a taper-lock structure. In particular, the backside of the head is provided with a male or female taper, and a mating structure is provided on the top of the stem. After selecting the appropriate components, the surgeon places the head on the stem and drives the pieces together to lock them in place. Unfortunately, because the components are held together only by friction, it is possible for them to become loosened or dislocated after installation, in which case another operation must be performed to restore the implant.

Another drawback with taper-lock modular designs is that it can be difficult to disassemble an implant and install a new head without removing the stem from the bone. In particular, it is often difficult to impart enough force to the head to separate the taper-lock without dislodging the stem from the bone at the same time. Moreover, to be removed, the head must be lifted away from the stem by the length of the taper and, thus, the joint must be dislocated to permit the necessary separation. As a result, the recovery time is greatly extended over what would be required if dislocation were not necessary.

Another common feature of many existing taper-lock designs is a proximal flange attached to the top of the stem adjacent the head. This flange prevents the implant from subsiding down into the femur and avoids the resulting upward force on the bottom of the head which would tend to separate the taper lock. Unfortunately, over time, bony ingrowth can occur around the underside of the flange and the sides of the stem. Although this bony ingrowth is beneficial in that it helps to stabilize the implant, it also makes the implant much more difficult to remove when a revision is necessary. In particular, the flange blocks the surgeon from slipping a chisel down the bone adjacent the sides of the implant to separate the implant from the bone. As a result, a significant amount of bone may be dislodged with the implant, making it more difficult to secure the replacement implant.

The flanges used on many implants are also problematic because they decrease the thickness available for the head. The natural humeral head is typically 16–18 mm thick. Typical flanges are around 3 mm thick and, with a taper-lock device, a gap of approximately 2 mm must be left between the bottom of the head and the collar to accommodate the machining tolerances in the taper. As a result, the implant head is often significantly thinner than the original anatomy. This can limit joint mobility and increase the chance of dislocation.

In addition to the specific drawbacks associated with various existing implant designs, there are a number of general problems inherent in shoulder replacements. In particular, it is generally difficult to establish the proper position and orientation for the implant in the humerus. One of the more important variables is the rotational position, or retroversion, of the head on the humerus. Anatomically, the average retroversion between a plane defined by the perimeter of the anatomical head and the axis of the flexed forearm is approximately 30-degrees. Unfortunately, with existing implants and techniques for their installation, it has been very difficult to reliably reproduce desired retroversion. Establishing correct retroversion is important because incorrect retroversion can lead to problems with subsequent dislocation.

In addition to the retroversion of the implant, it is necessary to establish the correct height of the implant on the humeral shaft. With existing designs, the surgeon slips the stem into the medullary canal and makes an educated guess at the proper height. Excess height may create too much tension in the deltoid, while inserting the implant too far down the humerus can result in deltoid lag. Similarly, the offset of the face of the head relative to the stem must be established correctly or excess or insufficient tension in the rotator cuff may be created. Unfortunately, with existing designs there is no way to evaluate implant height or head offset prior to final installation, after which correction is difficult.

SUMMARY OF THE INVENTION

The present invention is a modular shoulder prosthesis including a head having a semi-spherical articulation surface bounded by an articular margin disposed in an articular plane generally normal to a head axis. The head further includes a backside disposed opposite the articulation surface and separated from the articulation surface by the articular margin. The prosthesis also includes a stem portion with a proximal end and a distal shaft for insertion into a medullary canal along a shaft axis. A coupling structure is adapted to removably attach the head to the stem through motion in the articular plane.

BRIEF DESCRIPTION OF THE FIGURES

FIGS. 4–9 are various views of a body portion of the implant of FIG. 1.

FIG. 17 is a medial elevational view of the implant of FIG. 1.

FIG. 21 is an isometric view of the implant of FIG. 1 in an assembled configuration.

DETAILED DESCRIPTION

Figure 1:
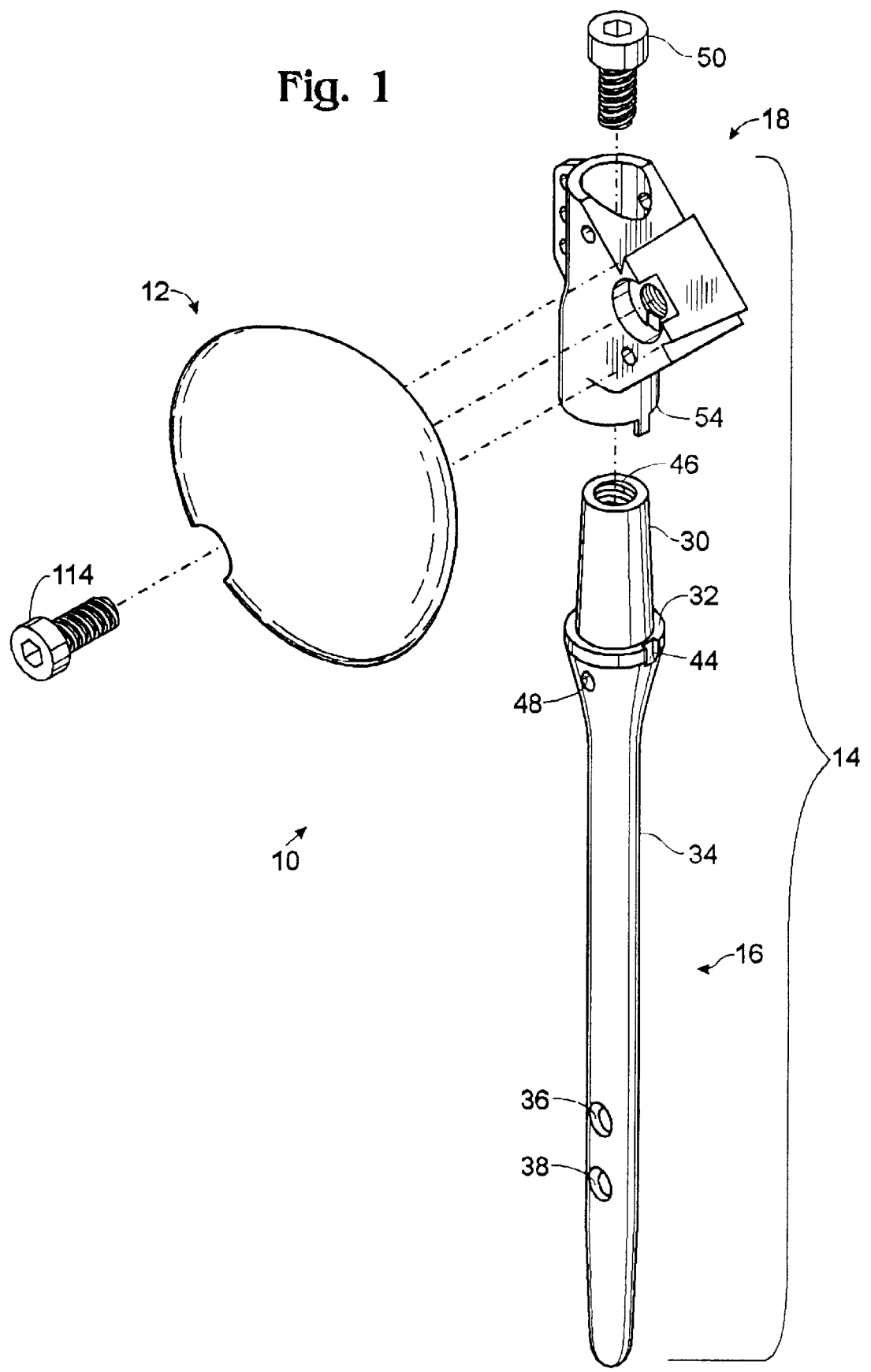
FIG. 1 is an exploded isometric view of a modular shoulder implant constructed according to the present invention.
Figure 2:
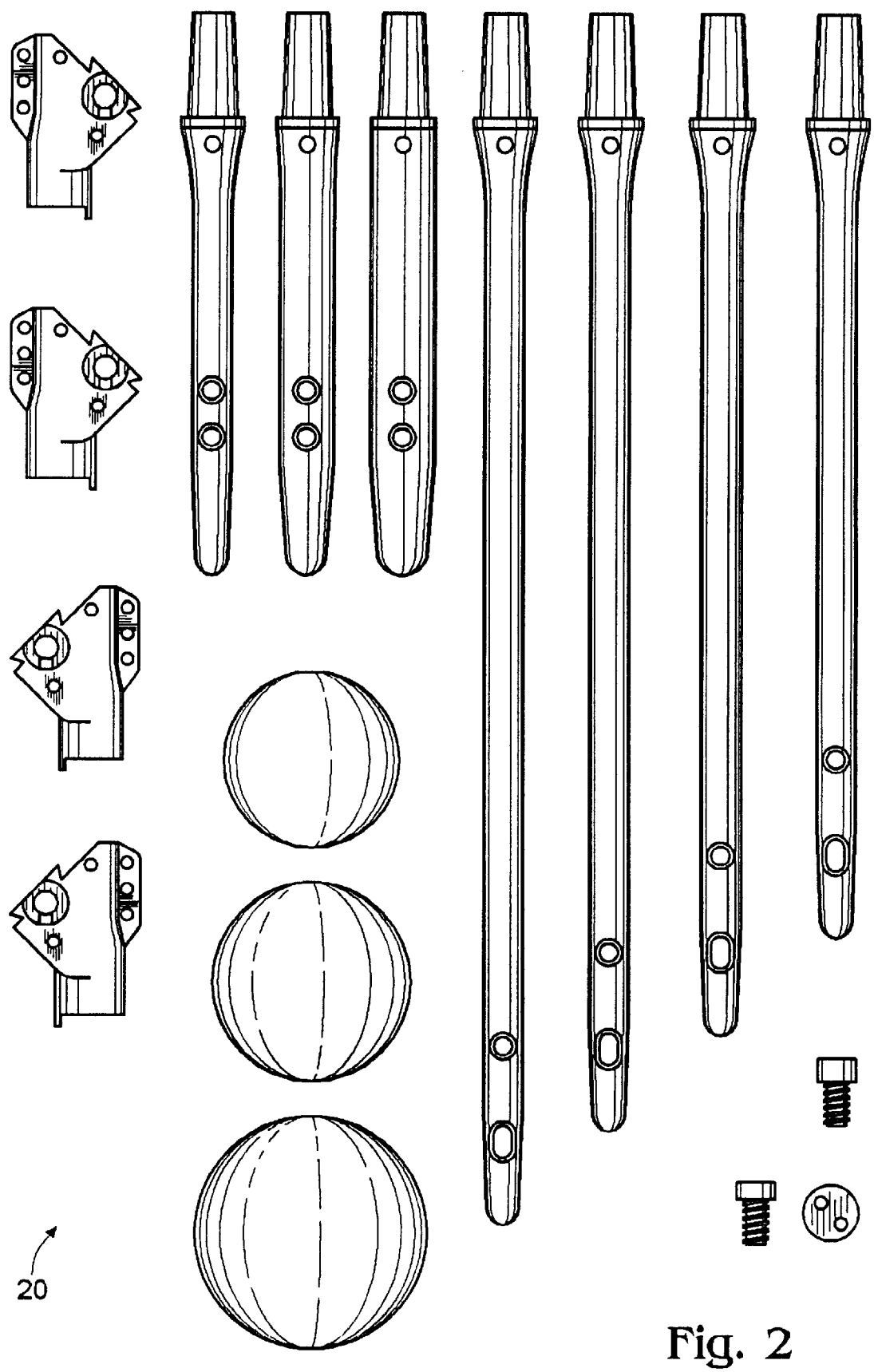
FIG. 2 shows a modular shoulder implant kit constructed according to the present invention.

A shoulder implant constructed according to the present invention is shown generally at 10 in FIG. 1. Implant 10 includes a head 12 and a stem 14. The stem preferably includes a distal shaft 16 and a body 18. The components making up implant 10 are preferably chosen from a kit 20 of interchangeable shafts, bodies and heads, as shown in FIG. 2. By selecting an appropriate shaft, body and head from kit 20, a surgeon is able to create an implant that is sized properly for almost any patient. It should be noted that positional references such as anterior/posterior, medial/ lateral and proximal/distal used herein are made with reference to an implant as it would be positioned in a patient.

Figure 3:
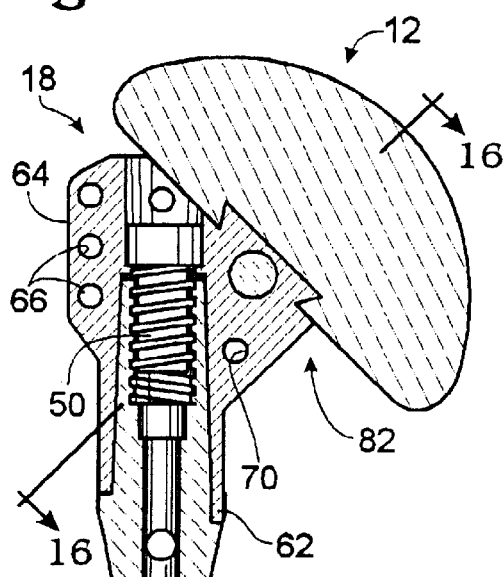
FIG. 3 is a cross-sectional view of a shaft of the implant of FIG. 1.

Shaft 16 is shown in greater detail in FIG. 3 and includes a proximal tapered end 30 extending distally to a shoulder 32 which tapers smoothly into a cylindrical medial region 34 with distal locking holes 36, 38. As can be seen in FIG. 2, the shaft can have a medial region of varying diameter and/or varying length. Generally speaking, the longer shafts are used where there is a mid-shaft fracture in addition to the proximal trauma. The varying diameter short shafts are used to accommodate size variations in the proximal end of the humerus. Either or both of holes 36, 38 may be elongated to allow for movement of the medial region over the locking screws. This is normally desirable when the implant is used to treat a combined mid-shaft fracture.

A rounded and tapered distal tip 40 is formed on the end of medial region 34. Shaft 16 preferably includes a central canulation 42 which can be used to guide the implant into the humerus with the aid of a guide wire. As best shown in FIG. 1, an alignment notch 44 is formed in shoulder 32 to aid in establishing the correct orientation of the body on the shaft, as will be described below. A threaded hole 46 is formed in tapered end 30 to receive a screw 50 which is used to draw the body firmly onto the tapered end. A wiring hole 48 is provided just distal of shoulder 32 to allow tension band wiring to be secured through the implant. In addition, when the implant is to be cemented in place, a K-wire can be driven through humerus and hole 48 to fix the position of the implant while the cement cures.

As indicated in FIG. 1, body 18 mounts to the top of shaft 16. Referring to FIGS. 4–9, body 18 has a distal end 54 with a cylindrical tapering socket 56 extending upwardly therefrom into the body. Socket 56 is sized to receive tapered end 30 of shaft 16 and taper-lock thereto to allow the body to be securely mounted to the shaft. A proximal bore 58 extends from the socket to the top of the body to the previously discussed screw to engage the top of the shaft to draw it into the socket. A small rib 60 is provided in the bore to engage against the head of the screw.

A small finger 62 projects down from the distal end of body 18 adjacent the socket to engage alignment notch 44 as the body is installed on the shaft. See FIGS. 1 and 17. This ensures the proper rotational positioning of the body on the shaft so that the various holes in the shaft are oriented correctly. Body 18 further includes a lateral rib 64 with three suture holes 66 which aid in securing the fracture fragments to the implant. Upper and lower medial suture holes 68, 70 are also provided in body 18 to offer additional options in securing the fragments. A medially-positioned, anteriorly-oriented threaded hole 72 is formed in body 18 to receive a screw for securing the head to the body. Hole 72 also serves as a mounting point for a targeting/installation instrument used with the implant. A recess 74 is located at the top of the hole and includes a keying notch 76 for orienting the targeting/installation instrument. See FIGS. 1 and 4. The recess allows the screw head to install substantially flush with the surface of the body to minimize the amount of bone removal required to insert the stem into the humerus.

Body 18 includes a medially-facing inclined mounting surface 80 at the proximal end onto which head 12 is mounted. Head 12 is secured to body 18 by coupling structure 82 which includes a fitting in the form of a pedestal or dovetail 84 located on mounting surface 80. As shown in FIGS. 6 and 8, dovetail 84 is tapered from anterior to posterior to establish a taperlock with the head, as will be described below. Because the dovetail is tapered, the body has a left or right orientation depending on which shoulder is to be replaced. Thus, as shown in FIG. 2, the kit will preferably include two or more bodies. Additional bodies, over and above one left and one right, may be provided to accommodate different stem diameters or head angles, etc.

Head 12, which is preferably formed as a unitary member, as opposed to being assembled from two or more components, includes a generally semi-spherical articulation surface 90 which is adapted to engage the glenoid cavity in the shoulder. See FIGS. 10–13. Because the glenoid cavity does not define a close fitting socket, such as found in the acetabulum in the hip joint, the articulation surface only needs to be sufficiently spherical to allow smooth articulation in the glenoid cavity.

Figure 14:
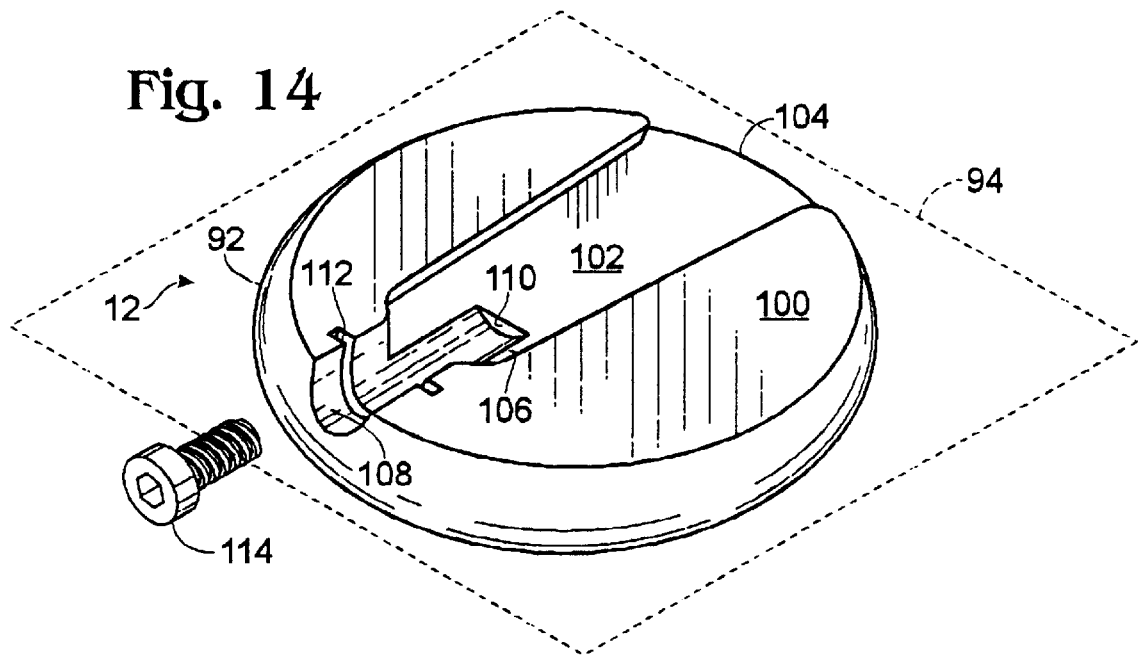
FIG. 14 is an isometric view of the backside of the head of FIGS. 10–13.

As best shown in FIG. 14, articulation surface 90 is bounded by an articular margin 92 which defines an articular plane 94 generally normal to a head axis 96. In the preferred embodiment, where the head is substantially spherical, the head axis represents a central axis of rotational symmetry for the articulation surface and a center of curvature 98 lies on the head axis. See FIG. 11. As shown by the dotted lines in FIG. 13, the various heads are preferably formed with the same radius, but simply represent larger portions of a sphere. It is believed that this best reflects the actual anatomical characteristics.

In the most commonly occurring fracture pattern, the anatomic head fractures generally through the articular margin and plane. The articular plane defines generally the distal extent of head 12. This is important when it is necessary to remove the head as part of a revision procedure, because the present invention allows the head to be removed from an anterior direction without dislocation of the joint and the associated trauma. This is not the case with existing implant heads, which cannot be separated from the body for removal without first dislocating the joint. It is desirable, although not required, that the head not project substantially beyond the articular plane in the present invention so that it is possible to slide the head out of the joint in an anterior direction without disruption of the surrounding bone. Because the remainder of the humerus is distal to the articulation plane, the head may be slid out in that plane without disruption of the surrounding bone as long as the head does not project substantially beyond the articular plane. Thus, the coupling structure is adapted to allow the head to be installed on and removed from the stem without dislocating the shoulder after the implant has been installed in the shoulder.

Head 12 includes a mounting surface or backside 100 disposed opposite the articulation surface and separated from the articulation surface by the articular margin. Backside 100 includes a portion of coupling structure 82 in the form of a transverse track or undercut channel 102. Channel 102 is cut to match the cross-sectional shape and taper of dovetail 84 and includes an open end 104 and an inner end 106. A cylindrical recess 108 extends from the perimeter of the head past the inner end of the channel and to a stop 110. A groove 112 is formed in recess 108 near the edge of the head.

The channel is sized so that the head is guided onto the body and the dovetail taperlocks in the channel when the head is properly positioned. See FIG. 10. The taperlock connection is important because it rigidly secures the components and prevents them from fretting against each other and generating debris over time. The coupling structure of the present invention may also be described as a transversely acting taper lock, with a portion of the taper lock being disposed on the head and a portion disposed on the body. The taper lock of the present invention is transverse acting in that it does not rely on motion along the axis of the head to lock, contrary to existing designs. In fact, it can be seen that, when the head is engaged on the stem, the coupling structure mechanically interlocks the head against motion transverse to the articular plane. This is in contrast to existing designs, which simply rely on a frictional interconnection in the direction transverse to the articular plane.

Figure 16:
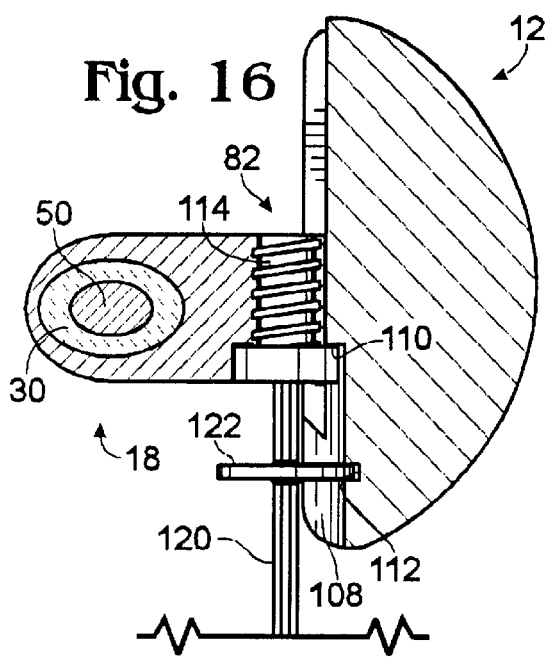
FIG. 16 is a cross-sectional view of the implant along line 8—8 of FIG. 3.
Figure 15:
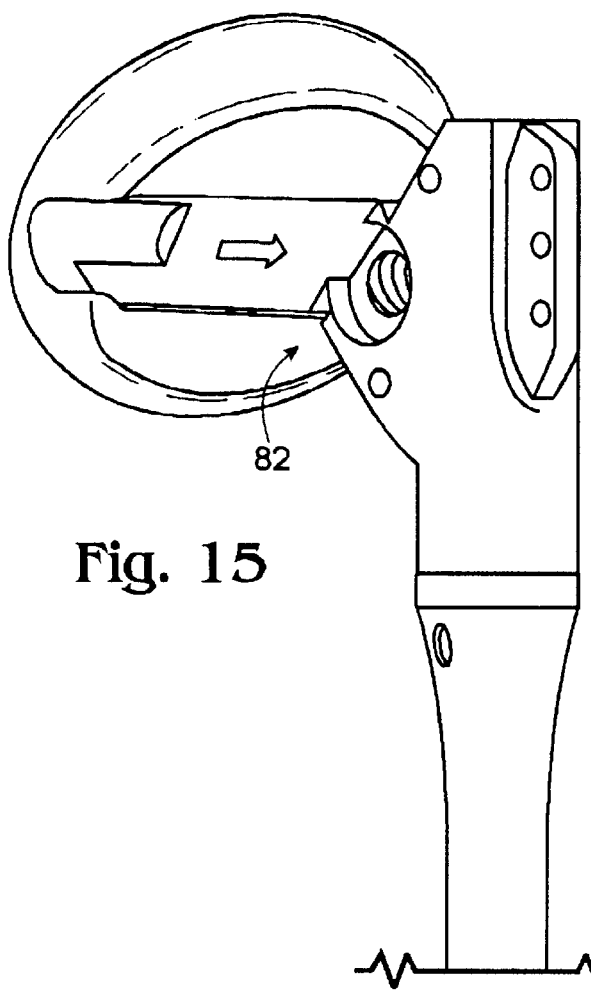
FIG. 15 is an isometric view of the head partially installed on the body.
Figure 10:
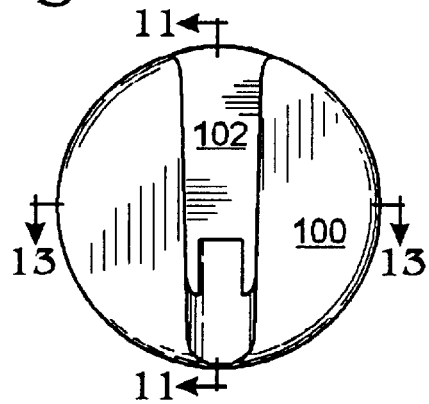
FIGS. 10–13 are various views of a head portion of the implant of FIG. 1.
Figure 11:
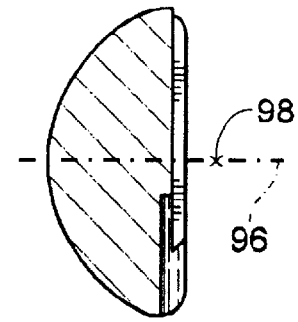
Figure 12:
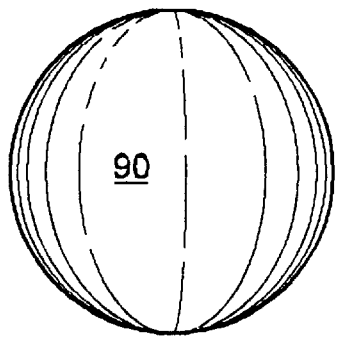
Figure 13:
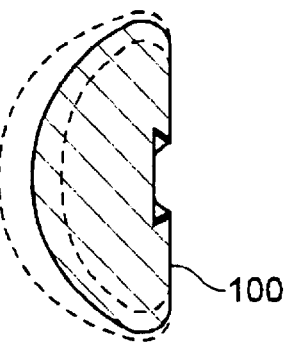

A locking member in the form of a screw 114 is provided to draw the head firmly onto the body to properly seat the taperlock. In particular, after head 12 is initially positioned on the body, as shown in FIG. 15, it is slid generally into position and screw 114 is installed into hole 72 with the head of the screw fitting closely into cylindrical recess 108. See FIG. 16. As the screw is driven in, the head of the screw engages stop 110 to pull head 12 firmly onto body 18. Screw 114 also serves as a backup interlock to insure that the head does not become dislodged. It should be noted that the head of the screw will not seat completely against the body because some space must be left to accommodate machining tolerances in the coupling structure so that the taper lock may be drawn tight in all cases.

When it is necessary to remove the head, as in a revision, a tool 120 with a flange 122 secured near the tip of the tool is utilized. See FIG. 16. The tip of the tool is initially installed in the screw head from a slight angle away from the head and then the tool is rotated toward the head to engage the flange with taper breaking surface in the form of a groove 112 formed in recess 108. As the screw is backed out, the flange pulls against the head to dislodge the taperlock. Thus, the head can be removed with application of external force to the implant, as has been required with prior designs. This reduces the chance that the entire implant will be loosened when only the head needs to be removed.

Figure 18:
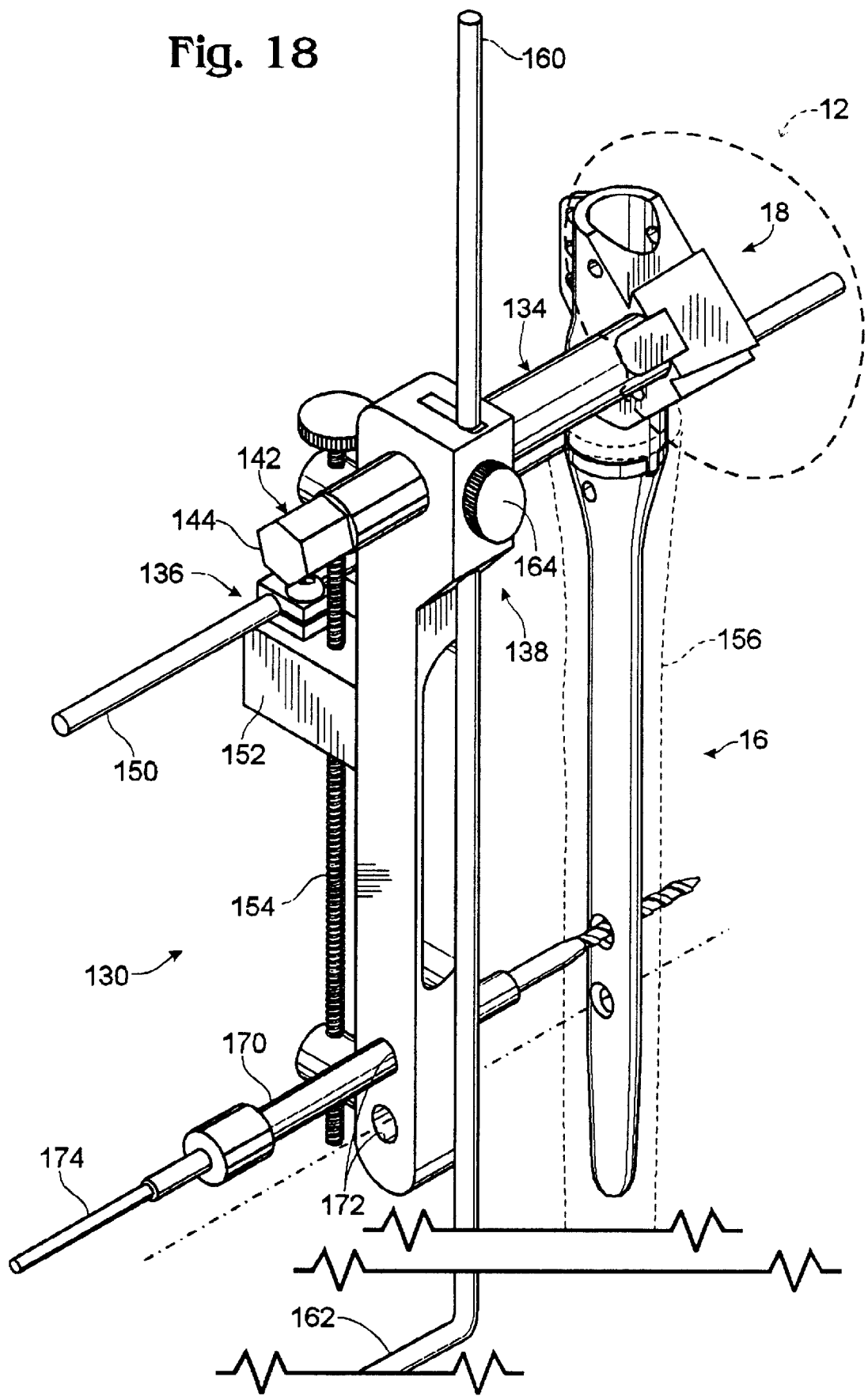
FIG. 18 is an isometric view of a targeting/installation instrument according to the present invention.

Installation of the implant of the present invention is facilitated by a targeting/installation instrument, shown generally at 130 in FIG. 18. Instrument 130 includes a template member 132 to which are mounted a mounting bar 134, a height adjusting mechanism 136 and a retroversion guide 138. Mounting bar 134 serves to join template member 132 to implant 10. In particular, bar 134 is hollow and includes a tab 140 (not shown) at the free end. The bar receives a bolt 142 with a head 144 and a threaded end 146. To attach the instrument to the implant, the free end of the bar is placed in recess 74 and aligned so that tab 140 fits into keying notch 76. This establishes the correct alignment between the template and the implant. The threaded end of the bolt is then screwed into hole 72 to secure the instrument to the implant. The bar includes a flat 148 to allow the bar to reach body 18 without engaging head 12. In addition, it should be noted that the screw which secures the head to the body is not installed until after the instrument is removed.

Once the instrument is mounted to the implant, the stem is inserted into the shaft of the humerus. In the typical fracture pattern, the head and greater and lesser tubercles are separated from the remainder of the humerus, leaving a pipe-like upper shaft. As a result, there is no remaining reference for the correct height of the implant head relative to the top of the humeral shaft. It is important to position the head at the correct height relative to the humeral shaft to avoid excess tension on the deltoid muscle by having the head too high or deltoid lag where the head is too low and the deltoid must undergo some contraction prior to starting to move the arm.

Figure 19:
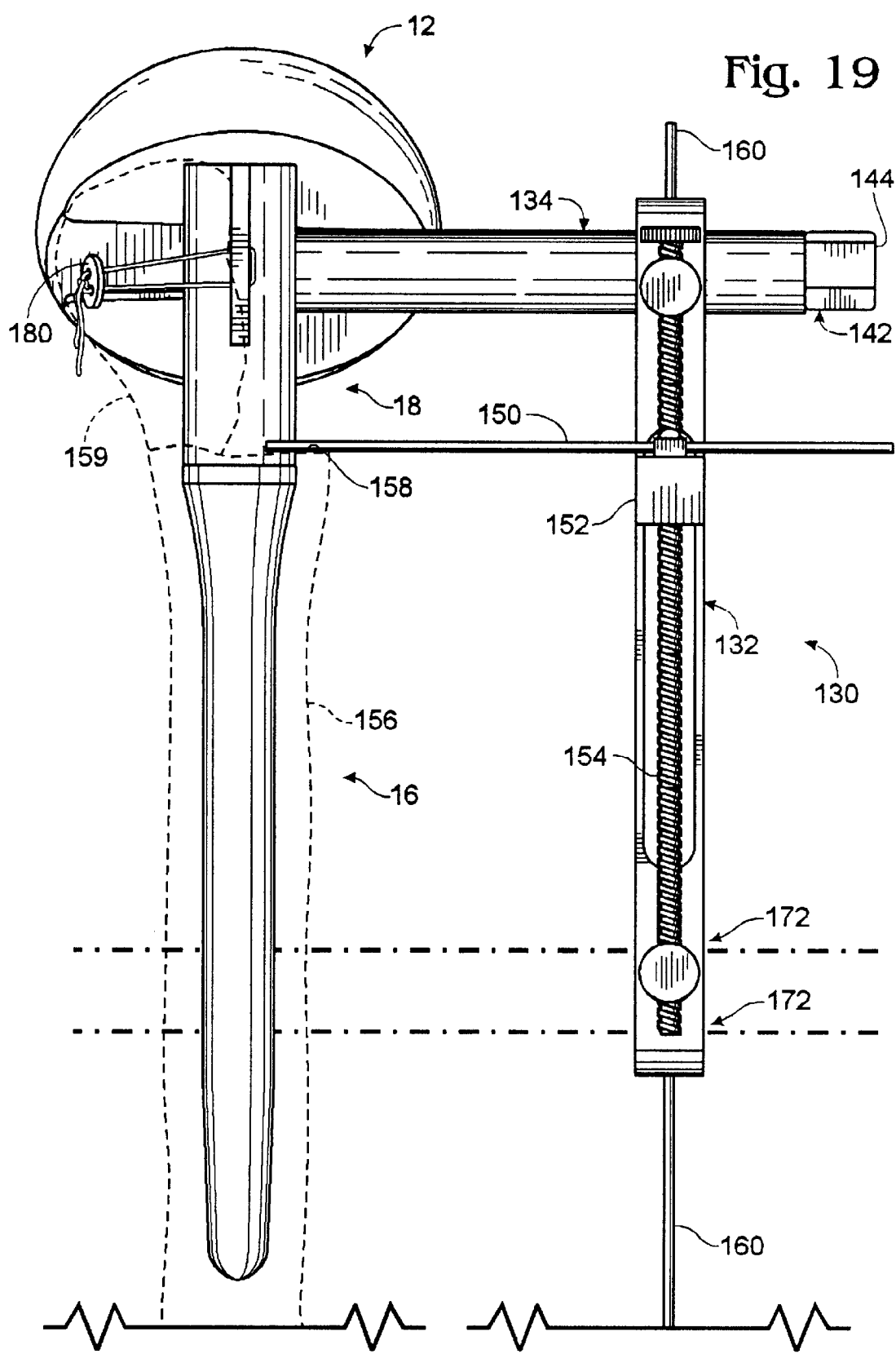
FIG. 19 is a lateral elevational view of the targeting/ installation instrument of FIG. 10.

The height adjusting mechanism allows the surgeon to temporarily set the height of the head and then evaluate the deltoid tension. In particular, as shown in FIGS. 18 and 19, height adjusting mechanism 136 includes a guide bar 150 which is moveably mounted to a carriage 152, which is driven up and down along a threaded rod 154. With the implant in a humeral shaft 156, the guide bar is positioned to sit on top 158 of the humeral shaft. The surgeon can then adjust the implant up or down by turning the threaded rod. The guide bar establishes a predetermined height, which can be maintained while retroversion is set and even if the implant is removed and reinserted, as when bone cement is used.

Figure 20:
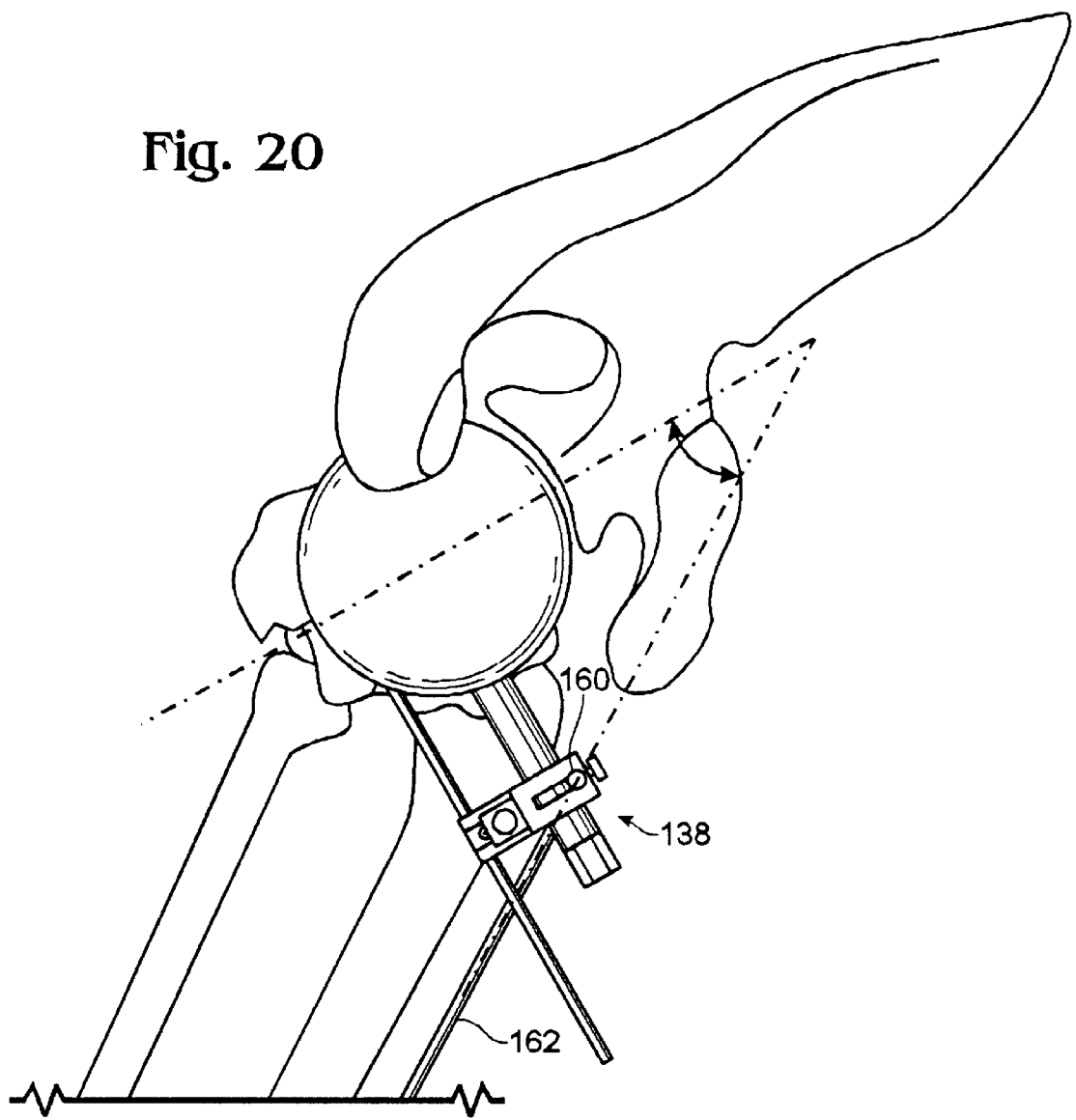
FIG. 20 is an elevational view from above of the targeting installation instrument of FIG. 18.

After establishing the correct height the surgeon can use the retroversion guide to set correct retroversion, as shown in FIG. 20. The retroversion guide includes an L-shaped rod 160 with a lower sighting arm 162. Rod 160 is pivotally and slidably mounted to template 132 to allow the height and angular orientation of the sighting arm to be adjusted. A set screw 164 allows the position of the rod to be fixed once it is in the desired orientation. In use, the sighting arm is set for a predetermined retroversion angle relative to the head axis, for instance 30-degrees. This can be accomplished before attachment to the implant using a protractor jig (not shown). With the sighting arm set to the correct orientation, the patient's forearm is flexed to approximately 90-degrees to the humerus. The surgeon then rotates the implant to align the sight arm with the axis of the forearm, thereby easily and accurately establishing the desired retroversion.

Once the correct height and retroversion is established, a cannulated drill guide 170 is inserted through guide holes 172 provided in the distal end of the template member. See FIG. 18. Guide holes 172 are oriented to target locking holes 36 in the end of the stem. A drill 174 is inserted though the drill guide to bore through the bone over the locking holes. One or two screws are installed through the humerus and locking holes to secure the implant in place.

As shown by the dotted lines in FIG. 19, it is possible to attach the greater tubercle 159 to the implant prior to final securing of the head. This allows the surgeon to evaluate the tension in the rotator cuff and make corrections, if necessary, by moving to a smaller or larger head. One other feature of the present invention is the provision of suture supports 180, shown in FIG. 21, which serve to distribute the force of the suture over the bone. Particularly in trauma cases, the bone is very soft and without supports 180, the sutures will sometimes pull through the bone. By utilizing the supports, the surgeon can obtain the desired suture tension without risk of the suture pulling through the surface of the bone.

It should be noted that the targeting/installation instrument is provided in left and right versions, although it would also be possible to make mounting bar 134 reversible or symmetric to accommodate left and right bodies. In addition, a longer template member would be used with the longer shafts used to treat mid-shaft fractures.

While the invention has been disclosed in its preferred form, it is to be understood that the specific embodiment thereof as disclosed and illustrated herein is not to be considered in a limiting sense as numerous variations are possible and that no single feature, function or property of the preferred embodiment is essential. The invention is to be defined only by the scope of the issued claims.

I claim:

1. A shoulder prosthesis comprising:
   a head having a semi-spherical articulation surface shaped to articulate with a glenoid cavity and bounded by an articular margin disposed in an articular plane generally normal to a head axis, the head further including a backside disposed opposite the articulation surface and separated from the articulation surface by the articular margin;
   a stem portion including a proximal end and a distal shaft for insertion into a medullary canal along a shaft axis; and
   a coupling structure in the form of a transversely acting taper lock, with a first portion of the taper lock being mounted on the head and a second portion of the taper lock being mounted on the proximal end of the stem, the taper lock being adapted to tighten under motion generally transverse to the head axis.

2. The prosthesis of claim 1, wherein the stem portion further includes a separable body portion, where the body portion forms the proximal end of the stem.

3. The prosthesis of claim 1, wherein the stem portion is cannulated.

4. The prosthesis of claim 1, wherein the transversely acting taper lock includes a transversely oriented undercut channel and a mating pedestal that slideably engages the channel.

5. The prosthesis of claim 4, wherein the channel and pedestal are dovetail-shaped.

6. The prosthesis of claim 4, further including a selectively operable locking member associated with the coupling structure and adapted to tighten the taper lock upon operation.

7. The prosthesis of claim 4, wherein the pedestal is positioned on the proximal end of the stem and the channel is formed in the backside of the head.

8. The prosthesis of claim 1, wherein the stem has a central axis and the proximal end of the stem includes at least one transverse bore formed medial of the central axis for receipt of a suture.

9. The prosthesis of claim 1, further comprising a locking screw associated with the coupling structure to prevent the taper lock from disengaging when the screw is installed, the head having a taper breaking surface which the screw can selectively operate against upon removal of the screw to disengage the taper lock.

10. The prosthesis of claim 1, wherein the coupling structure is adapted to allow the head to be installed on and removed from the stem without dislocating the shoulder after the implant has been installed in the shoulder.

11. A shoulder prosthesis comprising:
    a unitary head having a semi-spherical articulation surface bounded by an articular margin disposed in an articular plane generally normal to a head axis, the head further including a backside disposed opposite the articulation surface and separated from the articulation surface by the articular margin,
    a stem portion including a proximal end and a distal shaft for insertion into a medullary canal along a shaft axis; and
    a coupling structure with an undercut track portion and a corresponding pedestal portion adapted to engage the undercut track for constrained motion along a coupling axis to a locked position, where one of the portions is incorporated in the head and one of the portions is incorporated in the stem with the coupling axis being oriented generally parallel to the articular plane.

12. The prosthesis of claim 11, wherein the coupling axis is further oriented transverse to the shaft axis.

13. The prosthesis of claim 11, wherein the stem portion further includes a separable body portion, where the body portion forms the proximal end of the stem portion.

14. The prosthesis of claim 11, wherein the track and pedestal portions are mutually tapered to establish a taper lock in the locked position.

15. A shoulder prosthesis comprising:
    a head having an articulation surface configured to articulate with the glenoid cavity and a backside opposed to the articulation surface;
    a stem portion including a proximal end and a distal shaft for insertion into a medullary canal along a shaft axis; and
    a coupling structure disposed partially on the backside of the head and partially on the proximal end of the stem portion and adapted to releasably couple the head to the proximal end of the stem portion, the coupling structure being configured to allow the head to be installed on and removed from the stem portion without shifting the head substantially away from the stem portion in the direction of the glenoid cavity.

16. The prosthesis of claim 15, wherein the coupling structure allows the head to be installed and removed from an anterior direction.

17. The prosthesis of claim 15, wherein the stem portion further includes a separable body portion, where the body portion forms the proximal end of the stem portion.

18. The prosthesis of claim 17, wherein the body includes a socket to receive a proximal tapered end of the distal shaft.

19. The prosthesis of claim 18, wherein the body includes an alignment member to establish a predetermined rotational orientation between the body and the shaft.

20. A shoulder prosthesis comprising:

a head having a semi-spherical articulation surface bounded by an articular margin disposed in an articular plane generally normal to a head axis, the head further including a backside disposed opposite the articulation surface and separated from the articulation surface by the articular margin;

a stem portion including a proximal end and a distal shaft for insertion into a medullary canal along a shaft axis; and a coupling structure disposed partially on the backside of the head and partially on the proximal end of the stem for guiding the head in a constrained motion along a coupling axis to a locked position, with the coupling axis being oriented generally transverse to both the head axis and the shaft axis.

21. The prosthesis of claim 20, wherein the stem portion further includes a separable body portion, where the body portion forms the proximal end of the stem portion.

22. The prosthesis of claim 21, wherein the portion of the coupling structure on the body is asymmetric relative to an anterior/posterior plane, whereby the body is particularly adapted for one side of a patient's body.

23. A shoulder prosthesis comprising:

a head having a semi-spherical articulation surface bounded by an articular margin disposed in an articular plane generally normal to a head axis, the head further including a backside disposed opposite the articulation surface and separated from the articulation surface by the articular margin;

a stem portion including a proximal end and a distal shaft for insertion into a medullary canal along a shaft axis; and a coupling structure disposed partially on the backside of the head and partially on the proximal end of the stem for releasably coupling the head to the stem; and a locking element configured to engage and interlock the head and the stem to prevent them from decoupling, the locking element being installable and removeable from an anterior direction without dislocating the shoulder.

24. The prosthesis of claim 23, wherein the head includes a recess to receive at least a portion of the locking element, the recess being oriented generally parallel to the articular plane to allow the locking element to be accessed after installation of the implant in the shoulder without significant disruption of bone around the prosthesis.

25. The prosthesis of claim 23, wherein, when the head is engaged on the stem, the coupling structure mechanically interlocks the head against motion transverse to the articular plane.

* * * * *